(12) United States Patent
Laurin

(10) Patent No.: US 6,685,811 B1
(45) Date of Patent: Feb. 3, 2004

(54) METHOD FOR SEPARATION OF MACROMOLECULES

(75) Inventor: Ylva Laurin, Uppsala (SE)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/787,940

(22) PCT Filed: Sep. 23, 1999

(86) PCT No.: PCT/SE99/01674

§ 371 (c)(1),
(2), (4) Date: May 16, 2001

(87) PCT Pub. No.: WO00/17631

PCT Pub. Date: Mar. 30, 2000

(30) Foreign Application Priority Data

Sep. 23, 1998 (SE) ................................................ 9803224

(51) Int. Cl.⁷ ..................... G01N 27/447; G01N 27/453
(52) U.S. Cl. ..................... 204/459; 204/465; 204/615; 204/610
(58) Field of Search ................ 204/450, 451, 204/462, 465, 600, 601, 613, 615, 459, 610

(56) References Cited

U.S. PATENT DOCUMENTS

| | | | |
|---|---|---|---|
| 4,971,670 A | 11/1990 | Faupel et al. ............... | 204/459 |
| 5,773,645 A | 6/1998 | Hochstrasser ............... | 204/456 |
| 6,013,165 A | * 1/2000 | Wiktorowicz et al. ....... | 204/456 |

FOREIGN PATENT DOCUMENTS

| | | | | |
|---|---|---|---|---|
| WO | WO 97/37216 | 10/1997 | ......... | G01N/27/447 |
| WO | WO 98/25135 | 6/1998 | ......... | G01N/27/447 |

* cited by examiner

*Primary Examiner*—T. Tung
*Assistant Examiner*—Alex Noguerola
(74) *Attorney, Agent, or Firm*—Royal N. Ronning, Jr.; Stephen G. Ryan; Yonggang Ji

(57) ABSTRACT

The invention relates to a method and a system, suitable for automation, for the, preferably preparative, separation of amphoteric macromolecules, e.g. proteins or peptides, wherein said method comprises the steps of: (a) subjecting said mixture of macromolecules to isoelectric focusing in liquid media; (b) collecting samples from step (a), said samples containing macromolecules separated on basis of isoelectric point, and transferring each sample to a channel (13) accommodating medium for electrophoresis, said channel (13) being part of a composite body (14); (c) subjecting said samples, contained in the channels (13) in said composite body (14), to electrophoresis; and (d) allowing electrophoresis to proceed until macromolecules are eluted from said medium for electrophoresis, and collecting fractions of the samples containing macromolecules.

16 Claims, 3 Drawing Sheets

METHOD FOR SEPARATION OF MACROMOLECULES

TECHNICAL FIELD

The present invention relates to methods for the separation, in particular, the preparative separation of amphoteric macromolecules by two-dimensional electrophoresis, whereby isoelectric focusing in liquid media is combined with electrophoresis, and subsequent electroelution to liquid media. The invention further relates to a system for separation of amphoteric macromolecules, comprising an isoelectric focusing unit, a composite body having channels accommodating the electrophoresis medium and an elution plate for use in said methods.

BACKGROUND ART

The principles for two-dimensional electrophoresis are known in the art. This technique has normally involved first subjecting a mixture of molecules to isoelectric focusing on a gel where a pH gradient has been established. As the molecules traverses the pH gradient they reach at some point a pH corresponding to their respective isoelectric point and stop migrating. Traditionally, this separation has been performed in a capillary gel, which then has been placed on top of a slab gel in order to subject the sample to SDS-PAGE, whereby the molecules are separated according to their molecular weights. In order to further process the separated molecules, additional handling steps are required, for example detecting the spots, cutting the gel pieces out of the slab gel and extraction of the material from the gel. A problem with this method is low recovery rates. Another problem with this method is that it is a largely manual procedure which requires skill to perform it and which is time-consuming to perform.

Isoelectric focusing can also be performed in liquid media, as disclosed in U.S. Pat. No. 4,971,670. A multi-chambered isoelectric focusing unit (IsoPrime™ unit) is commercially available. With this unit, a pH-graduated set of buffered polyacrylamide membranes separates a series of chambers through which a sample circulates. Each membrane defines a specified step in a pH gradient. Each chamber encompasses a pH (or pI) range determined by the pH values of the membranes that bound it. During electrophoresis, a protein passes through membranes into successive chambers until it reaches the chamber encompassing its pI. The protein remains focused in this chamber and can subsequently be recovered from the chamber. This process is intended to separate and purify one amphoteric compound from a flow of compound. It is not suitable for separating a plurality of compounds that are to be analysed and which have the same isoelectric point as all compounds having the same isoelectric point end up in the same chamber. They then have to be extracted from the chamber and further separated by some other means.

A composite body having channels suitable for accommodating gels for electrophoresis is disclosed in WO 97/37216. Said composite body comprises a wall structure made from integrally formed element having a plurality of parallel longitudinally extending channels, said channels accommodating chemical medium or media suitable for carrying out a test, analysis or reaction procedure in situ in the channels.

However, the presently known methods for separating mixtures of amphoteric macromolecules often requires multiple manual steps and are difficult to automate. In addition, the known methods are not optimised to prepare samples suitable for direct use in downstream applications, such as e.g. mass spectrometry.

SUMMARY OF THE INVENTION

The present invention provides a method for separating mixtures of amphoteric macromolecules which avoids the above mentioned drawbacks and is designed for automation. With the use of the methods according to the invention, samples are obtained in solution, ready for downstream processing by means of e.g. mass spectrometry or other characterisation methods.

Consequently, in a first aspect the invention provides a method for separating amphoteric macromolecules, e.g. proteins or peptides, comprising the steps (a) subjecting said mixture of macromolecules to isoelectric focusing in liquid media;

(b) collecting samples from step (a), said samples containing macromolecules separated on basis of isoelectric point, and transferring each sample to a channel accommodating medium for electrophoresis, said channel being part of a composite body;

(c) subjecting said samples, contained in the channels in said composite body, to electrophoresis; and (d) allowing electrophoresis to proceed until macromolecules are eluted from said medium for electrophoresis, and collecting fractions of the samples containing macromolecules.

DISCLOSURE OF THE INVENTION

The method according to the invention will be further described in the following sections, with reference to the mentioned steps (a) to (d):

(a) The Isoelectric Focusing Step

The isoelectric focusing step can conveniently be performed in a unit having a series of chambers separated by membranes, each chamber encompassing a pH range determined by said membranes. Such units are known in the art from e.g. U.S. Pat. No. 4,971,670. However, it will be understood that according to the present invention, said units and separation chambers can be considerably smaller than those known in the art. In the method according to the invention, a separation chamber can e.g. conveniently have a volume from about 50 to about 500 $\mu$l, preferably about 100 $\mu$l.

Figure 1:
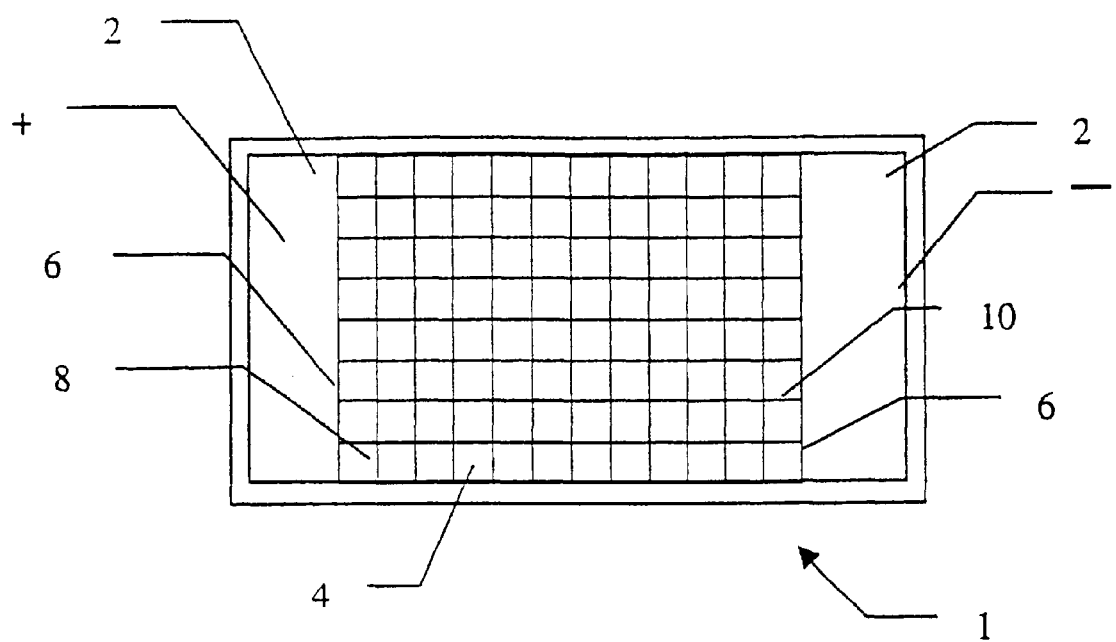
FIG. 1 is a schematic upper view of a device suitable for the first-dimension isoelectric focusing step.

In a preferred embodiment of the invention, the isoelectric focusing unit can be as schematically shown in FIG. 1. Such a unit, which in itself is a further aspect of the invention, can have the form and size of an ordinary microtitre plate (1) (normally about 15×85×125 mm). The plate (1) comprises a buffer chamber (2) at each short endand the anode (+) and cathode (−) can be placed or integrated in the buffer chambers. The plate has 8 rows and 12 columns of separation chambers (4), which are separated from the buffer chambers (2) by semi-permeable membranes (6) which have a suitable cut-off point (e.g. 2000 Da) to make them non-permeable to the macromolecules to be separated.

For isoelectric focusing, the biological sample, which normally contains from about 0.1 to 5 mg protein, is applied in one or more of the separation chambers (4), which are divided by membranes (8), preferably buffered polyacrylamide membranes, which each have a defined pH, thus defining a pH gradient, such as pH 3–10 or 4–7, along a row of separation chambers. The separation chambers (4) are filled with a buffer which normally will contain urea, a non-ionic detergent, carrier ampholytes and a reduction agent. A suitable buffer could e.g. contain 8 M urea; 4% CHAPS or 2% Triton-X100; 0.5 to 2% Pharmalyte® (Amersham Pharmacia Biotech, Uppsala, Sweden); and 60 mM dithiothreitol (DTT).

The 8 rows of separation chambers (4) are divided by walls (10) which run in the direction of the current, i.e. perpendicular to the pH-defined membranes (8), and which are non-permeable to the biological macromolecules to be separated.

Consequently, several distinct samples can be subjected to isoelectric focusing on one single plate without any risk that molecules will cross over from one row to another.

The isoelectric focusing is normally allowed to proceed for from 5.000 to 50.000 volt hours, depending on sample load and pH interval. During the isoelectric focusing step, each macromolecules in the biological sample migrates over the membranes (8) in the rows of separation chambers (4), until it reaches the chamber (4) which encompasses its pI. The molecule remains focused in this chamber (4).

(b) Transfer to the Electrophoresis Step

Figure 2:
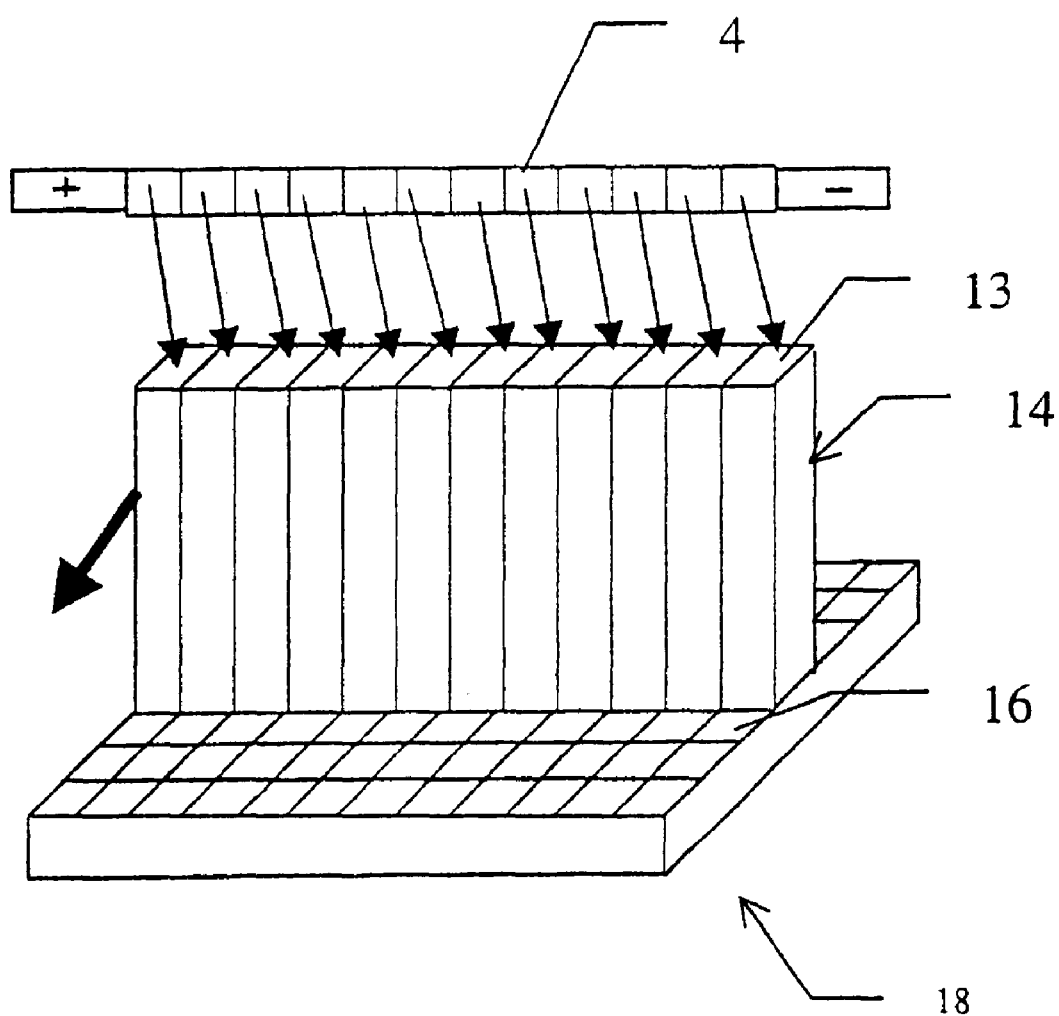
FIG. 2 is a schematic view of a composite body suitable for second-dimension electrophoresis and a collecting plate.

After isoelectric focusing, samples are collected, either manually or, preferably automatically using computer controlled multi-channel pipettes, by extracting the fluid from each of the separation chambers (4) in turn and transferring it to the channels (13) in the composite body (14) for electrophoresis. As illustrated in FIG. 2, the, for example, twelve samples collected from one row of separation chambers (4) can conveniently be transferred to the corresponding twelve channels (13) in a composite electrophoresis unit (14). Alternatively 8 samples from a column of eight separation chambers (4) can be transferred to 8 channels (13) in a composite electrophoresis unit (14). If necessary, suitable additives, such as SDS (sodium dodecyl sulphate), colour (e.g. brome phenol blue, BFB) and/or glycerol, can be added to the samples (c) The Electrophoresis Step The composite body (14) used for electrophoresis comprises a plurality of parallel longitudinally extending channels (13) suitable for accommodating electrophoresis media. In the present context the term "channels" is intended to include capillaries, as well as channels of a larger dimension. In the example shown in FIG. 2, the composite body (14) preferably has the same number of channels (13) as the number of separation chambers (4) in a row of separation chambers in plate (1), i.e. composite body (14) has twelve channels (13), However, composite body (14) can conceivably have any number of channels.

The composite body (14) can comprise e.g. parallel capillaries (13) that are attached together in a single line and regularly spaced. Alternatively, the composite body (14) can comprise a wall structure with longitudinally extending channels (13) in a single line. The channels can have circular, square or rectangular cross-sections, although other cross-sectional shapes are possible.

Said wall structure is preferably extruded from a synthetic material, such as glass or a plastic material, such as polypropylene. A suitable material is a commercially available polypropylene material, in the form of semi-rigid sheets, known as Correx™.

The chemical medium for electrophoresis may be uniform throughout the channels (13) or may vary in strength or concentration in a regular or other predetermined way across the array of channels. Different media may be accommodated in different channels. Also, the chemical medium may be arranged to vary, e.g. in concentration, along the length of the channel. The electrophoresis medium can be e.g. agarose, polyacrylamide, or another matrix forming medium.

Figure 4:
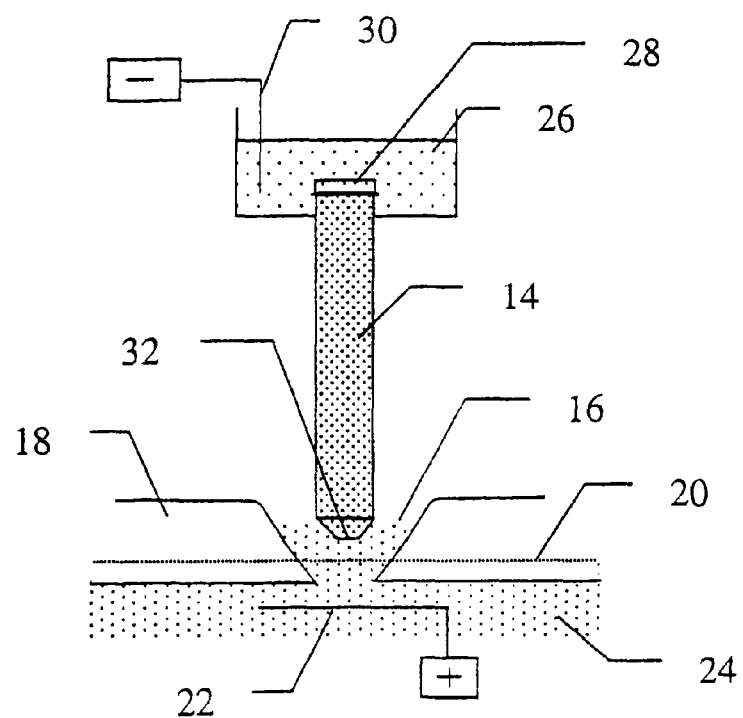
FIG. 4 is a side view of a channel filled with electrophoresis medium together with the upper buffer container and the collecting plate.

During electrophoresis, the composite body (14) is placed into contact with a container (26) in which the cathode (30) is placed or integrated, and which contains the upper electrophoresis buffer. Such a container (26) can e.g. have the form of a collar (26), which is tightly fitted to the upper part of the composite body (14) (FIG. 4). The buffer or buffers to be used in the electrophoresis step can be obtained by well known methods, e.g. as described by Laemmli (1970) Nature (London) 227, 680; or by Garfin, D. R., Methods Enzymol. Vol. 182, 425.

The electrophoresis step can be performed under with or without the addition of SDS (sodium dodecyl sulphate) to the samples and/or buffer. SDS is added to obtain denaturing conditions in standard SDS-PAGE, for the separation of macromolecules based on molecular weight, while addition of SDS has to be avoided e.g. for investigations of protein conformation, proteins interactions or protein-nucleic acid interactions.

(d) The Collection Step

When the electric field is applied in the electrophoresis arrangement, the negatively charged molecules migrate towards the anode (22) and can consequently be eluted and collected from the electrophoresis channels (13) by letting electrophoresis proceed until the samples have reached the end of the gels. At this stage, the macromolecules subject to electrophoresis have been further separated on e.g. the basis of molecular weight.

In a preferred form of the invention, the composite electrophoresis unit is dimensioned to allow for elution of samples from the channels (13) directly into wells (16) of a collecting plate (18) which can have the form and size of an ordinary microtitre plate. The collecting plate has a number of rows of wells (16) where the number of wells (16) in each row is the same as the number of channels (13) in the composite body (14). It will be understood that for this purpose, each of the electrophoresis channels (13) will have a protruding part (32) that will make sample delivery into discrete wells (16) on the collecting plate (18) possible.

Figure 3:
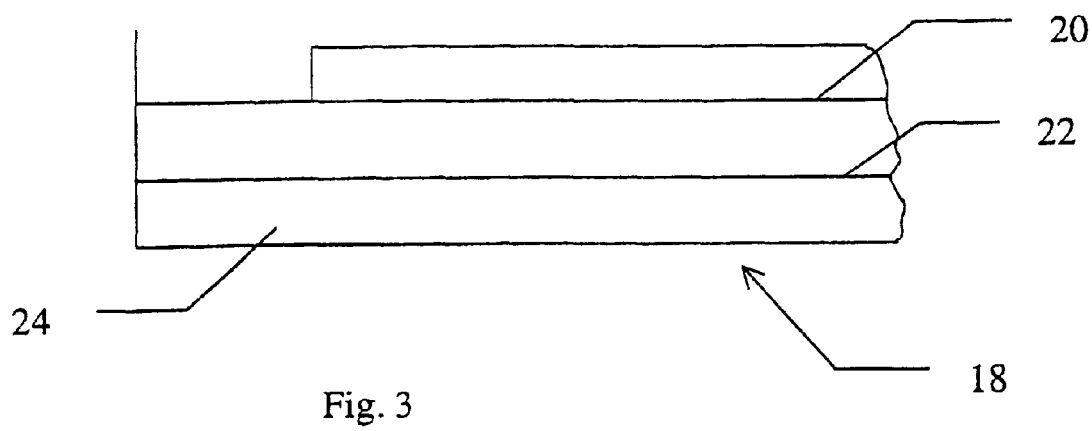
FIG. 3 is a side view of the lower buffer reservoir of the collecting plate.

Rather than having a solid bottom, as with ordinary microtitre plates, the collecting plate (18) is preferably fitted with a filter or semi-permeable membrane (20) which covers the open bottom of each well (16) and which has a suitable cut-off point (e.g. 2000 Da) to make it non-permeable to the macromolecules to be separated. This is schematically illustrated in FIG. 3, which is a partial side view of the lower buffer chamber (24), in which the anode (22) is placed or integrated.

FIG. 4 further schematically illustrates a suitable arrangement for electrophoresis and sample collection, including a channel (13) integrated in a composite electrophoresis unit (14) and harbouring electrophoresis medium. The composite unit is in contact with a container (26) in which the cathode (30) is placed or integrated, and which contains the upper electrophoresis buffer. The sample subject to electrophoresis is loaded in the space (28) between the top of the electrophoresis gel chamber encompassing a pH range determined by said membranes; (b) a composite body having channels accommodating gels for electrophoresis; and (c) a collecting plate. It will be understood that said system is adapted for automatically performing the methods according to the invention, and that the various parts of said system consequently have the preferred features described above.

Consequently, said isoelectric focusing unit preferably has at least one series of chambers separated by membranes, each chamber encompassing a pH range determined by said membranes, and has essentially the dimensions of a microtitre plate. Preferably it comprises a plurality of rows of separation chambers, said rows being divided by walls that are non-permeable to the macromolecules to be separated.

Preferably, said collecting plate essentially has the dimensions of a microtitre plate and said composite body has preferably dimensions that allow elution from the channels directly into the wells of such a collecting plate.

The collecting plate preferably comprises a semi-permeable membrane covering the bottom of each well, said membrane being non-permeable to the macromolecules to be collected.

What is claimed is:

1. A method, suitable for automation, for separation, especially preparative separation, of amphoteric macromolecules, comprising the steps of:
   (a) subjecting a mixture of amphoteric macromolecules to isoelectric focusing in liquid media;
   (b) collecting samples from step (a), said samples containing the macromolecules separated on basis of isoelectric point, and transferring each sample to a channel (13) accommodating medium for electrophoresis, said channel being part of a composite body (14);
   (c) subjecting said samples, contained in each of the channels (13) in said composite body (14), to electrophoresis; and
   (d) allowing electrophoresis to proceed until sample fractions in each channel resulting from the electrophoresis are eluted from the medium for electrophoresis, and collecting the eluted sample fractions.

2. The method of claim 1, wherein the isoelectric focusing step is performed in a unit (1) having at least one series of separation chambers (4) separated by membranes (8), each chamber encompassing a pH range determined by said membranes (8).

3. The method of claim 2, wherein said unit (1) essentially has the dimensions of a microtitre plate.

4. The method of claim 2, wherein said unit (1) comprises a plurality of rows of separation chambers (4), said rows being divided by walls (10) which are non-permeable to the macromolecules to be separated.

5. The method of claim 1, wherein said composite body (14) is in contact with a container (26) harbouring a cathode (30) and electrophoresis buffer.

6. The method of claim 1, wherein samples from the electrophoresis channels (13) are eluted directly into wells (16) on a collecting plate (18).

7. The method of claim 6, wherein said collecting plate (18) essentially has the dimensions of a microtitre plate, and said composite body (14) has dimensions which allows for elution from the channels (13) directly into the wells (16) of said collecting plate (18).

8. The method of claim 6, wherein said collecting plate (18) comprises a semi-permeable membrane (20) covering the bottom of each well (16), said membrane (20) being non-permeable to the macromolecules to be collected.

9. The method of claim 6, wherein during a first time portion of the elution, a first sample fraction from one channel (13) is eluted in a first well (16) of said collecting plate; during a second time portion of the elution, a second sample fraction is eluted into a second well (16) of said collecting plate; and during an nth time portion of the elution, an nth sample fraction is eluted into the nth well (16) of said collecting plate (18).

10. The method of claim 1, wherein one or more steps is/are carried out automatically by a robot.

11. The method of claim 1, comprising using an isoelectric focusing unit having at least one series of separation chambers (4) separated by membranes (8), each separation chamber (4) encompassing a pH range determined by said membranes (8), wherein said isoelectric focusing unit essentially has the dimensions of a microtitre plate.

12. The method of claim 11, wherein the isoelectric focusing unit comprises a plurality of rows of said series of separation chambers (4), said rows being divided by walls (6) which are non-permeable to the macromolecules to be separated.

13. The method of claim 1, comprising using a system for separating amphoteric macromolecules having:
   (a) a means for isoelectric focusing, including a unit having a series of separation chambers (4) separated by membranes (8), each separation chamber (4) encompassing a pH range determined by said membranes (8);
   (b) a composite body (14) having channels (13) accommodating gels for electrophoresis; and
   (c) a collecting plate (18).

14. The system of claim 13, wherein said composite body (14) is in contact with a container (26) harbouring a cathode (30) and electrophoresis buffer.

15. The system of claim 13, wherein said collecting plate (18) essentially has the dimensions of a microtitre plate and said composite body (14) has dimensions which allows for elution from the channels (13) directly into the wells (16) of a said collecting plate (18).

16. The system of claim 15, wherein said collecting plate (18) comprises a semi-permeable membrane (20) covering the bottom of each well (16), said membrane (20) being non-permeable to the macromolecules to be collected.

* * * * *